United States Patent
Schneider et al.

(10) Patent No.: US 11,773,042 B2
(45) Date of Patent: Oct. 3, 2023

(54) PROCESS FOR HYDROFORMYLATION OF OLEFINS USING PT AND IODINE

(71) Applicant: EVONIK OPERATIONS GMBH, Essen (DE)

(72) Inventors: Carolin Schneider, Monheim am Rhein (DE); Ralf Jackstell, Rostock (DE); Matthias Beller, Ostseebad Nienhagen (DE); Robert Franke, Marl (DE)

(73) Assignee: EVONIK OPERATIONS GMBH, Essen (DE)

( * ) Notice: Subject to any disclaimer, the term of this patent is extended or adjusted under 35 U.S.C. 154(b) by 0 days.

(21) Appl. No.: 18/064,946

(22) Filed: Dec. 13, 2022

(65) Prior Publication Data

US 2023/0192582 A1 Jun. 22, 2023

(30) Foreign Application Priority Data

Dec. 17, 2021 (EP) .................... 21215350

(51) Int. Cl.
  *C07C 45/50* (2006.01)
  *B01J 27/13* (2006.01)
  *B01J 31/24* (2006.01)
  *B01J 37/04* (2006.01)

(52) U.S. Cl.
  CPC ......... *C07C 45/505* (2013.01); *B01J 31/2457* (2013.01); *B01J 37/04* (2013.01); *B01J 2231/321* (2013.01); *B01J 2531/828* (2013.01)

(58) Field of Classification Search
  CPC ...... C07C 45/505; B01J 27/13; B01J 31/1845
  See application file for complete search history.

(56) References Cited

PUBLICATIONS

Botteghi. C. et al. Synthesis of 2-chromanol by hydroformylation of 2-hydroxystyrene derivatives. Journal of Molecular Catalysis A: Chemical 200. 2003. pp. 147-156.
U.S. Appl. No. 18/064,945, filed Dec. 13, 2022, Schneider et al.
U.S. Appl. No. 18/064,947, filed Dec. 13, 2022, Schneider et al.
U.S. Appl. No. 18/064,948, filed Dec. 13, 2022, Schneider et al.
U.S. Appl. No. 18/064,949, filed Dec. 13, 2022, Schneider et al.
U.S. Appl. No. 18/064,950, filed Dec. 13, 2022, Schneider et al.
U.S. Appl. No. 18/064,952, filed Dec. 13, 2022, Schneider et al.
U.S. Appl. No. 18/064,953, filed Dec. 13, 2022, Schneider et al.
U.S. Appl. No. 18/064,955, filed Dec. 13, 2022, Schneider et al.
U.S. Appl. No. 18/064,958, filed Dec. 13, 2022, Schneider et al.
European Search Report dated Jun. 17, 2022 for European Patent Application No. 21215350.6 (5 pages in German with Machine Translation).
Petöcz, G., et al. Xantphos as cis- and trans-chelating ligand in square-planar platinum(II) complexes. Hydroformylation of styrene with platinum-xantphos-tin(II)chloride system. Journal of Organometallic Chemistry. 2004. vol. 689, No. 7, pp. 1188-1193.
Translation of the Saudi Arabia Office Action received Jun. 27, 2023 for Saudi Arabia Application No. 122440758(1). (4 pages).
Zhang, Y. et al. Binuclear Pd(I)—Pd(I) Catalysis Assisted by Iodide Ligands for Selective Hydroformylation of Alkenes and Alkynes. American Chemical Society. 2020. vol. 142, pp. 18251-18265.
Duren, van, R. Platinum catalyzed hydroformylation. Phd Thesis 1 (Research TU/e / Graduation TU/e), Chemical Engineering and Chemistry. Technische Universiteit Eindhoven. 2004. 119 pages.

*Primary Examiner* — Sikarl A Witherspoon
(74) *Attorney, Agent, or Firm* — Smith, Gambrell & Russell, LLP

(57) ABSTRACT

Process for hydroformylation of olefins using Pt and iodine.

15 Claims, No Drawings

PROCESS FOR HYDROFORMYLATION OF OLEFINS USING PT AND IODINE

The present invention relates to a process for hydroformylation of olefins using Pt and iodine.

C. Botteghi et al., Journal of Molecular Catalysis A: Chemical 200, (2003), 147-156 describes the use of Pt(Xantphos)Cl$_2$ for hydroformylation of 2-tosyloxystyrene.

The problem addressed by the present invention is that of providing a novel hydroformylation process. The process here is to afford an increased yield compared to the process known from the prior art using Pt(Xantphos)Cl$_2$.

This object is achieved by a process according to Claim 1.

Process comprising the process steps of:
a) initially charging an olefin;
b) adding a compound of formula (I):

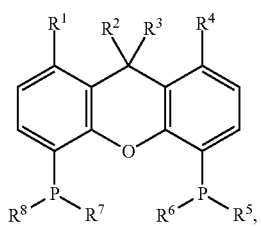

(I)

where R$^1$, R$^2$, R$^3$, R$^4$, R$^5$, R$^6$, R$^7$, R$^8$ are selected from: —H, —(C$_1$-C$_{12}$)-alkyl, —(C$_6$-C$_{20}$)-aryl; and, if R$^1$, R$^2$, R$^3$, R$^4$, R$^5$, R$^6$, R$^7$, R$^8$ are —(C$_6$-C$_{20}$)-aryl, the aryl ring may have substituents selected from: —(C$_1$-C$_{12}$)-alkyl, —O—(C$_1$-C$_{12}$)-alkyl;

c) adding a Pt compound capable of forming a complex;
d) adding an iodine compound;
e) feeding in CO and H$_2$;
f) heating the reaction mixture from steps a) to e), to convert the olefin to an aldehyde.

In this process, process steps a) to e) can be effected in any desired sequence. Typically, however, CO and H$_2$ are added after the co-reactants have been initially charged in steps a) to d).

It is possible here for process steps c) and d) to be effected in one step, by adding PtI$_2$. In a preferred variant of the process, the Pt compound and the iodine compound are added in one step, by adding PtI$_2$.

The expression (C$_1$-C$_{10}$-alkyl encompasses straight-chain and branched alkyl groups having 1 to 12 carbon atoms. These are preferably (C$_1$-C$_8$-alkyl groups, more preferably (C$_1$-C$_6$)-alkyl, most preferably (C$_1$-C$_4$)-alkyl.

Suitable (C$_1$-C10-alkyl groups are especially methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The expression (C$_6$-C$_{20}$-aryl encompasses mono- or polycyclic aromatic hydrocarbyl radicals having 6 to 20 carbon atoms. These are preferably (C$_6$-C$_{14}$)-aryl, more preferably (C$_6$-C$_{10}$)-aryl.

Suitable (C$_6$-C$_{20}$-aryl groups are especially phenyl, naphthyl, indenyl, fluorenyl, anthracenyl, phenanthrenyl, naphthacenyl, chrysenyl, pyrenyl, coronenyl. Preferred (C$_6$-C$_{20}$)-aryl groups are phenyl, naphthyl and anthracenyl.

In one variant of the process, R$^2$, R$^3$, R$^5$, R$^6$, R$^7$, R$^8$ are selected from: —(C$_1$-C10-alkyl, —(C$_6$-C$_{20}$-aryl.

In one variant of the process, R$^5$, R$^6$, R$^7$, R$^8$ are —(C$_6$-C$_{20}$-aryl.

In one variant of the process, R$^5$, R$^6$, R$^7$, R$^8$ are —Ph.

In one variant of the process, R$^2$ and R$^3$ are —(C$_1$-C10-alkyl.

In one variant of the process, R$^2$ and R$^3$ are —CH$_3$.

In one variant of the process, R$^1$ and R$^4$ are —H.

In one variant of the process, the compound (I) has the structure (1):

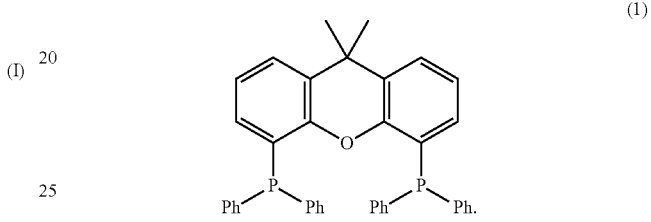

(1)

In one variant of the process, the Pt compound is selected from: Pt(II)I$_2$, Pt(IV)I$_4$, diphenyl(1,5-COD)Pt(II), Pt(II)(acac)$_2$, Pt(0)(PPh$_3$)$_4$, Pt(0)(DVTS) solution (CAS: 68478-92-2), Pt(0)(ethylene)(PPh$_3$)$_2$, tris(benzylideneacetone)Pt(0), Pt(II)(OAC)$_2$ solution, Pt(0)(t-Bu)$_2$, Pt(II)(COD)Me$_2$, Pt(II)(COD)I$_2$, Pt(IV)IMe$_3$, Pt(II)(hexafluoroacetylacetonate)$_2$.

In one variant of the process, the Pt compound is selected from: Pt(II)I$_2$, Pt(II)(acac)$_2$.

In one variant of the process, the iodine compound is selected from: alkali metal halide, alkaline earth metal halide, NH$_4$X, alkylammonium halide, dialkyl halide, trialkyl halide, tetraalkyl halide, cycloalkylammonium halide.

In one variant of the process, the iodine compound is selected from: Pt(II)I$_2$, LiI.

In one variant of the process, the iodine compound is added in an amount in the range of 0.1 to 10, measured in equivalents based on Pt.

In one variant of the process, this process comprises the additional process step e'): e') adding a solvent.

In one variant of the process, the solvent is selected from: THF, DCM, ACN, heptane, DMF, toluene, texanol, pentane, hexane, octane, isooctane, decane, dodecane, cyclohexane, benzene, xylene, Marlotherm, propylene carbonate, MTBE, diglyme, triglyme, diethyl ether, dioxane, isopropanol, tert-butanol, isononanol, isobutanol, isopentanol, ethyl acetate.

In one variant of the process, the solvent is selected from: THF, DCM, ACN, heptane, DMF, toluene, texanol.

In one variant of the process, CO and H$_2$ are fed in at a pressure in a range from 1 MPa (10 bar) to 6 MPa (60 bar).

In one variant of the process, CO and H$_2$ are fed in at a pressure in a range from 1 MPa (20 bar) to 6 MPa (50 bar).

In one variant of the process, the reaction mixture is heated to a temperature in the range from 25° C. to 150° C.

In one variant of the process, the reaction mixture is heated to a temperature in the range from 30° C. to 130° C.

In one variant of the process, the olefin is selected from: ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl- 2-butene, hexene, tetramethylethylene, heptene, 1-octene, 2-octene, di-n-butene, or mixtures thereof.

The invention shall be elucidated in more detail hereinbelow with reference to working examples.

EXPERIMENTAL DESCRIPTION

A vial was charged with $PtX_2$ (X=halogen), ligand, and an oven-dried stirrer bar. The vial is then sealed with a septum (PTFE-coated styrene-butadiene rubber) and phenolic resin cap. The vial is evacuated and refilled with argon three times. Toluene and olefin were added to the vial using a syringe. The vial was placed in an alloy plate, which was transferred to an autoclave of the 4560 series from Parr Instruments under an argon atmosphere. After purging the autoclave three times with $CO/H_2$, the synthesis gas pressure was increased to 40 bar at room temperature. The reaction was conducted at 120° C./80° C. for 20 h/18 h. On termination of the reaction, the autoclave was cooled to room temperature and cautiously decompressed. Yield and selectivity were determined by GC analysis.

Variation of the Metal

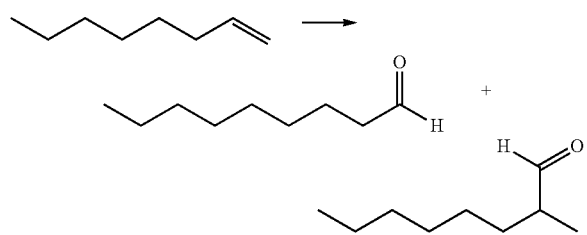

Reaction conditions:

20 mmol of 1-octene, 0.1 mol % of metal, 2.2 equivalents of Xantphos (1), solvent: toluene, $p(CO/H_2)$: 40 bar, T: 80° C., t: 20 h.

Yields:
$PtI_2$: 99%
$PdI_2$: 0%

Variation of the Halogen (2-octene)

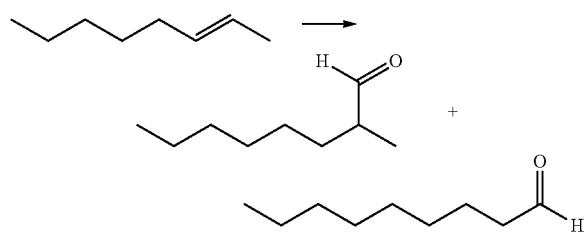

Reaction conditions:

20 mmol of 2-octene, 1.0 mol % of Pt, 1.1 equivalents of Xantphos (1), solvent: toluene, $p(CO/H_2)$: 40 bar, T: 120° C., t: 20 h.

Yields:
$PtI_2$: 99%
$PtCl_2$: 16%

Variation of the Halogen (1-octene)

Reaction conditions:

10.0 mmol of 1-octene, 0.1 mol % of $PtX_2$, 2.2 equivalents of ligand, solvent: toluene, $p(CO/H_2)$: 40 bar, T: 120° C., t: 20 h.

Yields:

| Ligand | Halogen | Yield [%] |
|---|---|---|
| (1) Xantphos structure | I/Cl | 99/5 |

Variation of the Olefin

Reaction conditions:

1.0 mmol of olefin, 0.5 mol % of $PtI_2$, 2.2 equivalents of Xantphos (1), solvent: dichloromethane (DCM), $p(CO/H_2)$: 40 bar, T: 80° C., t: 18 h.

Yields:

| Aldehyde | Yield [%] |
|---|---|
| nonanal | 99 |
| nonanedial / 9-oxononanoic acid | 99 |
| 3-phenylpropanal | 99 |
| 4-methylhexanal | 99 |

The C—C bond in bold indicates the position of the former double bond, i.e. the double bond in the olefin.

Variation of the Ligand and of the Halogen

Reaction conditions:

1.0 mmol of 1-octene, 0.5 mol % of $PtX_2$, 2.0 equivalents of ligand, solvent: toluene, $p(CO/H_2)$: 40 bar, T: 80° C., t: 18 h.

Yields:

| Ligand | Halogen | Yield [%] |
|---|---|---|
| (1) Xantphos (Ph₂P-xanthene-PPh₂) | I/Cl | 99/0 |
| (tol)₂P-xanthene-P(tol)₂ | I/Cl | 99/0 |
| (2-MeO-C₆H₄)(Ph)P-xanthene-P(Ph)(2-MeO-C₆H₄) | I/Cl | 99/<1 |
| (2-tol)(Ph)P-xanthene-P(Ph)(2-tol) | I/Cl | 95/0 |

Variation of the Equivalents and of the Halogen

Reaction conditions:

1.0 mmol of 1-octene, 1.0 mol % of $Pt(acac)_2$, LiX (X=halogen), 2.2 equivalents of Xantphos (1), solvent: toluene, $p(CO/H_2)$: 40 bar, T: 120° C., t: 20 h.

| Equivalents of LiX | X | Yield [%] |
|---|---|---|
| 0.5 | I | 99 |
| 1.0 | I | 99 |
| 2.0 | I | 99 |
| 4.0 | I | 99 |
| 4.0 | Cl | 0 |

As the experimental results show, the object is achieved by the process according to the invention.

The invention claimed is:
1. A process comprising the process steps of:
   a) initially charging an olefin;
   b) adding a compound of formula (I):

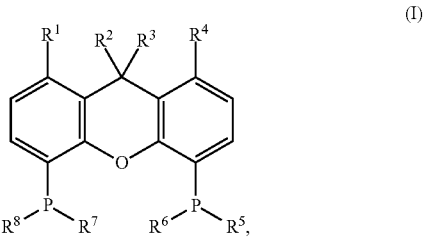

where $R^1$, $R^2$, $R^3$, $R^4$, $R^5$, $R^6$, $R^7$ and $R^8$ are selected from: —H, —($C_1$-$C_{12}$)-alkyl or —($C_6$-$C_{20}$)—aryl;
and, if $R^1$, $R^2$, $R^3$, $R^4$, $R^5$, $R^6$, $R^7$ and $R^8$ are —($C_6$-$C_{20}$)-aryl, the aryl ring may have substituents selected from: —($C_1$-$C_{12}$)-alkyl or —O—($C_1$-$C_{12}$)-alkyl;
   c) adding a Pt compound capable of forming a complex;
   d) adding an iodine compound;
   e) feeding in CO and $H_2$;
   f) heating the reaction mixture from steps a) to e), to convert the olefin to an aldehyde.

2. The process according to claim 1, where $R^2$, $R^3$, $R^5$, $R^6$, $R^7$ and $R^8$ are selected from: —($C_1$-$C_{12}$)-alkyl or —($C_6$-$C_{20}$)-aryl.

3. The process according to claim 1, where $R^5$, $R^6$, $R^7$ and $R^8$ are —($C_6$-$C_{20}$)-aryl.

4. The process according to claim 1, where $R^2$ and $R^3$ are —($C_1$-$C_{12}$)—alkyl.

5. The process according to claim 1, where $R^1$ and $R^4$ are —H.

6. The process according to claim 1, wherein the compound (I) has the structure (1):

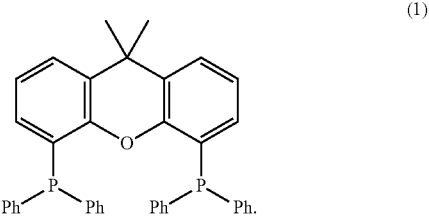 [SMILES: CC1(C)c2cccc(P(c3ccccc3)c3ccccc3)c2Oc2c(P(c3ccccc3)c3ccccc3)cccc21]

7. The process according to claim 1, wherein the Pt compound is selected from: $Pt(II)I_2$, $Pt(IV)I_4$, diphenyl(1,5-COD)Pt(II), $Pt(II)(acac)_2$, $Pt(0)(PPh_3)_4$, Pt(0)(DVTS) solution (CAS: 68478-92-2), Pt(0)(ethylene)(PPh3)2, tris(benzylideneacetone)Pt(0), $Pt(II)(OAC)_2$ solution, $Pt(0)(t-Bu)_2$, $Pt(II)(COD)Me_2$, $Pt(II)(COD)I_2$, $Pt(IV)IMe_3$ or Pt(II)(hexafluoroacetylacetonate)₂.

8. The process according to claim 1, wherein the Pt compound is selected from: Pt(II)I$_2$ or Pt(II)(acac)$_2$.

9. The process according to claim 1, wherein the iodine compound is selected from: Pt(II)I$_2$ or LiI.

10. The process according to claim 1, wherein the iodine compound is added in an amount in the range of 0.1 to 10, measured in equivalents based on Pt.

11. The process according to claim 1, comprising the additional process step e'):

e') adding a solvent.

12. The process according to claim 11, wherein the solvent is selected from: THF, DCM, ACN, heptane, DMF, toluene, texanol, pentane, hexane, octane, isooctane, decane, dodecane, cyclohexane, benzene, xylene, Marlotherm, propylene carbonate, MTBE, diglyme, triglyme, diethyl ether, dioxane, isopropanol, tert-butanol, isononanol, isobutanol, isopentanol or ethyl acetate.

13. The process according to claim 1, wherein CO and H$_2$ are fed in at a pressure in a range from 1 MPa (10 bar) to 6 MPa (60 bar).

14. The process according to claim 1, wherein the reaction mixture is heated to a temperature in the range from 25° C. to 150° C.

15. The process according to claim 1, wherein the olefin is selected from: ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene or mixtures thereof.

* * * * *